(12) United States Patent
Yokoi

(10) Patent No.: US 12,144,663 B2
(45) Date of Patent: Nov. 19, 2024

(54) X-RAY CT APPARATUS AND CORRECTION METHOD OF PROJECTION DATA

(71) Applicant: FUJIFILM Healthcare Corporation, Kashiwa (JP)

(72) Inventor: Kazuma Yokoi, Kashiwa (JP)

(73) Assignee: FUJIFILM Corporation, Tokyo (JP)

( * ) Notice: Subject to any disclaimer, the term of this patent is extended or adjusted under 35 U.S.C. 154(b) by 308 days.

(21) Appl. No.: 17/959,732

(22) Filed: Oct. 4, 2022

(65) Prior Publication Data
US 2023/0200757 A1  Jun. 29, 2023

(30) Foreign Application Priority Data
Dec. 28, 2021 (JP) ................. 2021-214549

(51) Int. Cl.
*A61B 6/00* (2024.01)
*A61B 6/03* (2006.01)
*A61B 6/58* (2024.01)
*G01N 23/046* (2018.01)

(52) U.S. Cl.
CPC ............. *A61B 6/032* (2013.01); *A61B 6/582* (2013.01); *G01N 23/046* (2013.01)

(58) Field of Classification Search
CPC .................................................... A61B 6/583
See application file for complete search history.

(56) References Cited

U.S. PATENT DOCUMENTS

| | | | | |
|---|---|---|---|---|
| 2010/0272319 A1* | 10/2010 | Oohara | ............... | A61B 6/542 |
| | | | | 382/106 |
| 2013/0026353 A1* | 1/2013 | Yan | ............... | A61B 6/583 |
| | | | | 250/252.1 |
| 2014/0064441 A1* | 3/2014 | Lou | ............... | G06T 11/006 |
| | | | | 378/5 |

OTHER PUBLICATIONS

Taly Gilat Schmidt et al., "A Spectral CT method to directly estimate basis material maps from experimental photon-counting data", IEEE Trans. Med. Imaging, vol. 36, No. 6, pp. 1808-1819, Sep. 2017.

* cited by examiner

*Primary Examiner* — Dani Fox
(74) *Attorney, Agent, or Firm* — Paul Teng

(57) ABSTRACT

An X-ray CT apparatus and a correction method of projection data that are capable of suppressing artifacts generated in the vicinity of an edge portion of a test subject are provided. The X-ray CT apparatus for photographing a test subject is characterized by comprising: a correction data creation unit that creates correction data using difference data between measurement projection data for each X-ray energy obtained by photographing a known phantom having a known composition, a known shape, and a size smaller than a photographing field of view of the X-ray CT apparatus and calculation projection data for each X-ray energy calculated on the basis of X-ray transmission lengths obtained from the shape of the known phantom; and a correction unit that corrects projection data for each X-ray energy of the test subject using the correction data.

7 Claims, 9 Drawing Sheets

X-RAY CT APPARATUS AND CORRECTION METHOD OF PROJECTION DATA

CLAIM OF PRIORITY

The present application claims priority from Japanese Patent Application JP 2021-214549 filed on Dec. 28, 2021, the content of which is hereby incorporated by reference into this application.

BACKGROUND OF THE INVENTION

The present invention relates to X-ray CT apparatuses and, in particular, relates to correction methods of projection data obtained by X-ray CT apparatuses.

Currently the development of PCCT (Photon Counting Computed Tomography) apparatuses equipped with photon counting type detectors, which are detectors that employ a photon counting scheme, has been under way. Since a photon counting type detector can measure X-ray energies that are the energies of incident X-ray photons, a medical image in which materials with different compositions are discriminated, for example, a medical image in which iodinated contrast agents used for angiography and calcified plaques in blood vessels are discriminated is obtained in a PCCT apparatus. Here, in order to obtain a medical image in which plural materials are discriminated, it is necessary to obtain relationships between outputs and X-ray energies in advance as calibration data for each of detection elements when a phantom composed of a combination of multiple base materials with known compositions and thicknesses is measured by a photon counting type detector.

"A Spectral CT method to directly estimate basis material maps from experimental photon-counting data", in IEEE Transactions on Medical Imaging, vol. 36, no. 6, pp. 1808-1819, September 2017 by Taly Gilat Schmidt et al. discloses that twenty-five types of calibration data are obtained by using stepped phantoms composed of 0 to 4 acrylic flat plates having a thickness of 2.54 cm and 0 to 4 aluminum flat plates having a thickness of 0.635 cm.

SUMMARY OF THE INVENTION

However, in the abovementioned nonpatent literature, consideration is not given to artifacts generated in the vicinity of the edge portion of a test subject. In other words, since the acrylic flat plates and the aluminum flat plates composing the stepped phantoms cover all detection elements, the influences of half shadows and scattered rays generated in the vicinity of the edge portion of the test subject cannot be grasped.

Therefore, an object of the present invention is to provide an X-ray CT apparatus and a correction method of projection data that are capable of suppressing artifacts generated in the vicinity of the edge portion of a test subject.

In order to accomplish the abovementioned object, the present invention is an X-ray CT apparatus for photographing a test subject, the X-ray apparatus including: a correction data creation unit that creates correction data using difference data between measurement projection data for each X-ray energy obtained by photographing a known phantom having a known composition, a known shape, and a size smaller than a photographing field of view of the X-ray CT apparatus and calculation projection data for each X-ray energy calculated on the basis of X-ray transmission lengths obtained from the shape of the known phantom; and a correction unit that corrects projection data for each X-ray energy of the test subject using the correction data.

In addition, the present invention is a correction method of projection data obtained by an X-ray CT apparatus for photographing a test subject, the correction method including the steps of: creating correction data using difference data between measurement projection data for each X-ray energy obtained by photographing a known phantom having a known composition, a known shape, and a size smaller than a photographing field of view of the X-ray CT apparatus and calculation projection data for each X-ray energy calculated on the basis of X-ray transmission lengths obtained from the shape of the known phantom; and correcting projection data for each X-ray energy of the test subject using the correction data.

According to the present invention, an X-ray CT apparatus and a correction method of projection data that are capable of suppressing artifacts generated in the vicinity of the edge portion of a test subject can be provided.

DETAILED DESCRIPTION OF THE PREFERRED EMBODIMENTS

Hereinafter, an embodiment of the present invention will be explained with reference to the accompanying drawings.

First Embodiment

Figure 1:
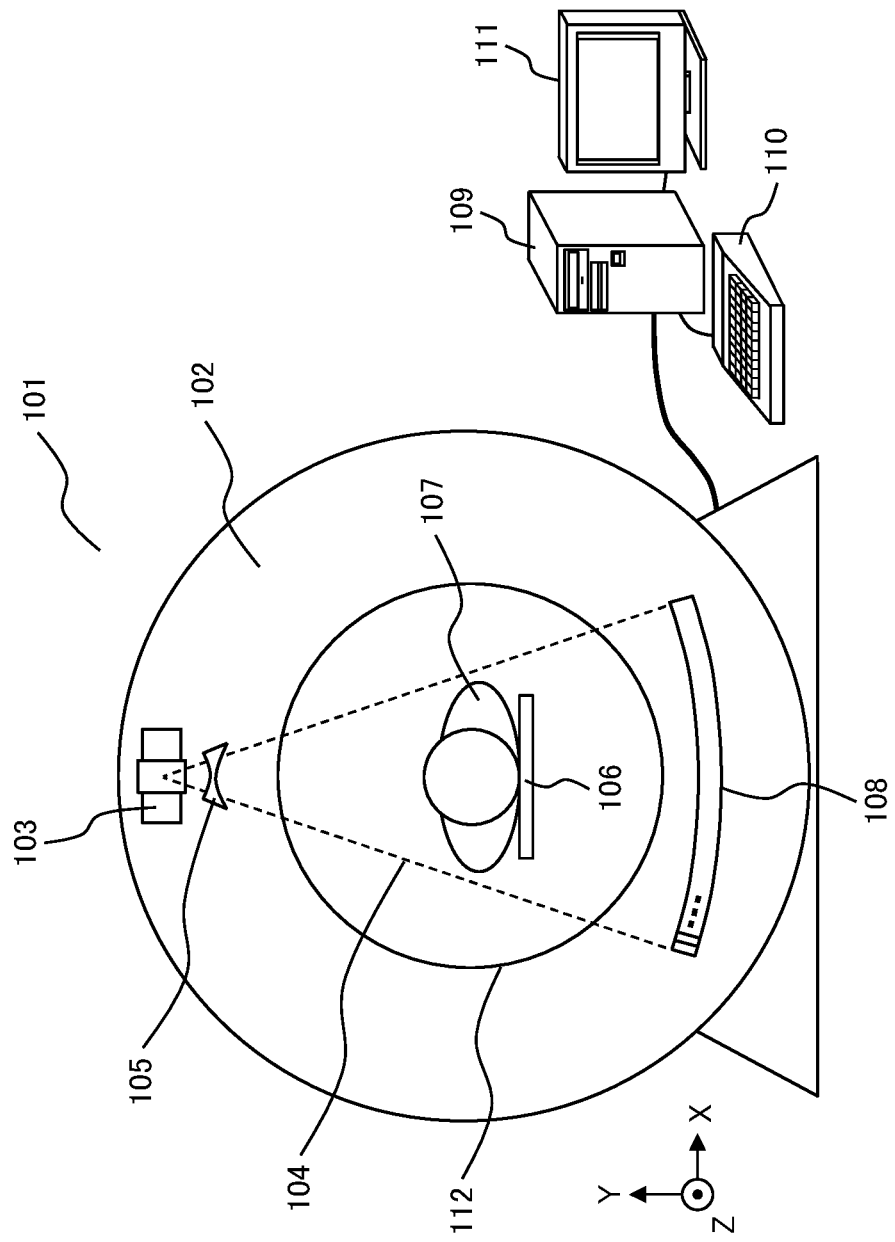
FIG. 1 is a diagram showing the overall configuration of an X-ray CT apparatus.

FIG. 1 shows an overall configuration of an X-ray CT apparatus 101 according to this embodiment. Here, it will be assumed that the horizontal direction of the paper surface is an X-axis direction, the vertical direction is a Y-axis direction, and the direction orthogonal to an XY plane is a Z-axis direction. The X-ray CT apparatus 101 includes: a gantry 102; an X-ray tube 103; a bow tie filter 105; a berth 106; a detector panel 108; an operation device 109; an input device 110; and a display device 111.

A test subject 107 is placed on the berth 106 and disposed in an opening 112 provided in the gantry 102. After X-rays 104 emitted from the X-ray tube 103 are formed into a beam shape suitable for the size of the test subject 107 by the bow tie filter 105, the X-rays 104 are irradiated to the test subject 107, and after the X-rays 104 are transmitted through the test subject 107, the X-rays 104 are detected by the detector panel 108. The X-ray tube 103 and the detector panel 108 are fixed to the gantry 102 in such a way that the X-ray tube 103 and the detector panel 108 are disposed opposite to each other with the test subject 107 therebetween, and the X-ray tube 103 and the detector panel 108 are rotated around the test subject 107 by the rotation driving unit of the gantry 102. By repeating the X-ray radiation from the X-ray tube 103 and the X-ray measurement at the detector panel 108 along with the rotation by the rotation driving unit, projection data at various projection angles is obtained.

Image reconstruction processing is performed on the obtained projection data by the operation device 109, so that the tomographic image of the test subject 107 is created and displayed on the display device 111. In addition, when projection data is acquired while the berth 106 on which the test subject 107 is placed and the gantry 102 move relatively in the Z-axis direction, a volume image of the test subject 107 is created. Here, an X-ray dose emitted from the X-ray tube 103, the rotation speed of the gantry 102, and a relative movement speed between the gantry 102 and the berth 106 are set on the basis of scan conditions inputted by an operator via the input device 110. Furthermore, the operation device 109 has a hardware configuration similar to that of a general computer device, includes a CPU (Central Processing Unit), a memory, an HDD (Hard Disk Drive), and the like, and performs correction processing on projection data and the like and controlling on respective units.

The detector panel 108 is configured by disposing plural detection elements in an arc shape with its center point at the X-ray focal point of the X-ray tube 103. Each of the detection elements is a photon counting type detector that measures an X-ray energy, which is the energy of incident X-ray photons, and detects an output corresponding to the X-ray energy.

Since the X-ray CT apparatus 101 including the photon counting type detectors can obtain X-ray energy spectra related to the projection data of the subject 107, it is possible to create a medical image in which materials having different compositions are discriminated or a medical image that is divided into plural medical images with different energy components. Here, in order to obtain a medical image in which materials with different compositions are discriminated and the like, it is necessary to calibrate in advance relationships between outputs and X-ray energies measured by each photon counting type detector for a combination of plural base materials having known compositions and known thicknesses for each detection element.

Figure 2:
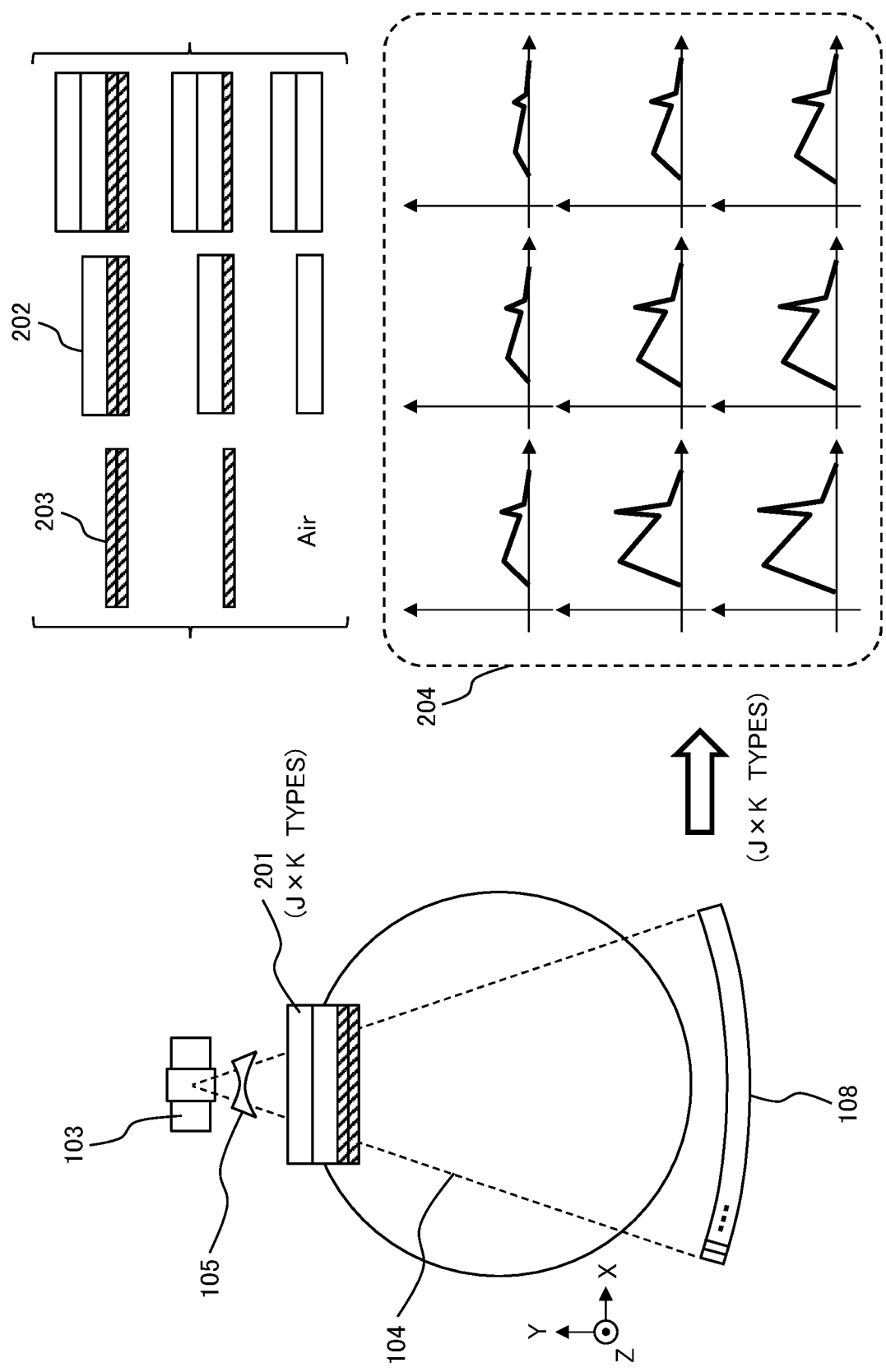
FIG. 2 is a diagram used for explaining the calibration of a photon counting type detector.

The calibration of a photon counting type detector will be explained with reference to FIG. 2. For the calibration of the photon counting type detector, calibration data 204, which is obtained using a combination of plural base materials with known compositions and thicknesses, for example, a combination 201 of two base materials, that is, a first base material 202 and a second base material 203, is used. As the first base material 202, a material having a relatively small effective atomic number such as acrylic or polyethylene is used. As the second base material 203, a material having a relatively large effective atomic number such as aluminum, hydroxyapatite, calcium mixture, iodine mixture, tin, or tin mixture is used. For a combination 201 of base materials, plural plates having different thicknesses may be used for each base material. For example, when combinations of plates made of the first base material 202 with J types of thicknesses and plates made of the second base material 203 with K types of thicknesses are considered, J×K types of combinations 201 of base materials are used, and an X-ray energy spectrum for each combination is obtained by each detection element. In FIG. 2, since J=3 and K=3, nine types of X-ray energy spectra are shown as calibration data 204.

The obtained calibration data 204 is memorized in the storage unit of the operation device 109, and used for the calibration of the projection data of the test subject 107.

Here, it is impossible to suppress artifacts that are generated in the vicinity of the edge portion of the test subject 107 with the use of only the calibration data 204 obtained using the combinations 201 of base materials. Therefore, in the first embodiment, the artifacts generated in the vicinity of the edge portion of the test subject 107 are suppressed by correcting the projection data of the test subject 107 using correction data created in advance. Here the correction data is created using difference data between measurement projection data for each X-ray energy obtained by photographing a known phantom having a known composition and a known shape and calculation projection data for each X-ray energy calculated on the basis of X-ray transmission lengths obtained from the shape of the known phantom.

An example of a processing flow of the first embodiment will be explained step by step with reference to FIG. 3.
(S301)
The operation device 109 obtains the projection data of the test subject 107 by controlling respective units on the basis of set scanning conditions. Since the detector panel 108 is composed of plural photon counting type detectors, projection data is obtained for each X-ray energy.
(S302)
The operation device 109 reads out the correction data used for the correction of the projection data obtained in S301. The correction data is created in advance on the basis of measurement projection data for each X-ray energy obtained by photographing a phantom having a known composition and a known shape, and memorized in the storage unit of the operation device 109.

Figure 4:
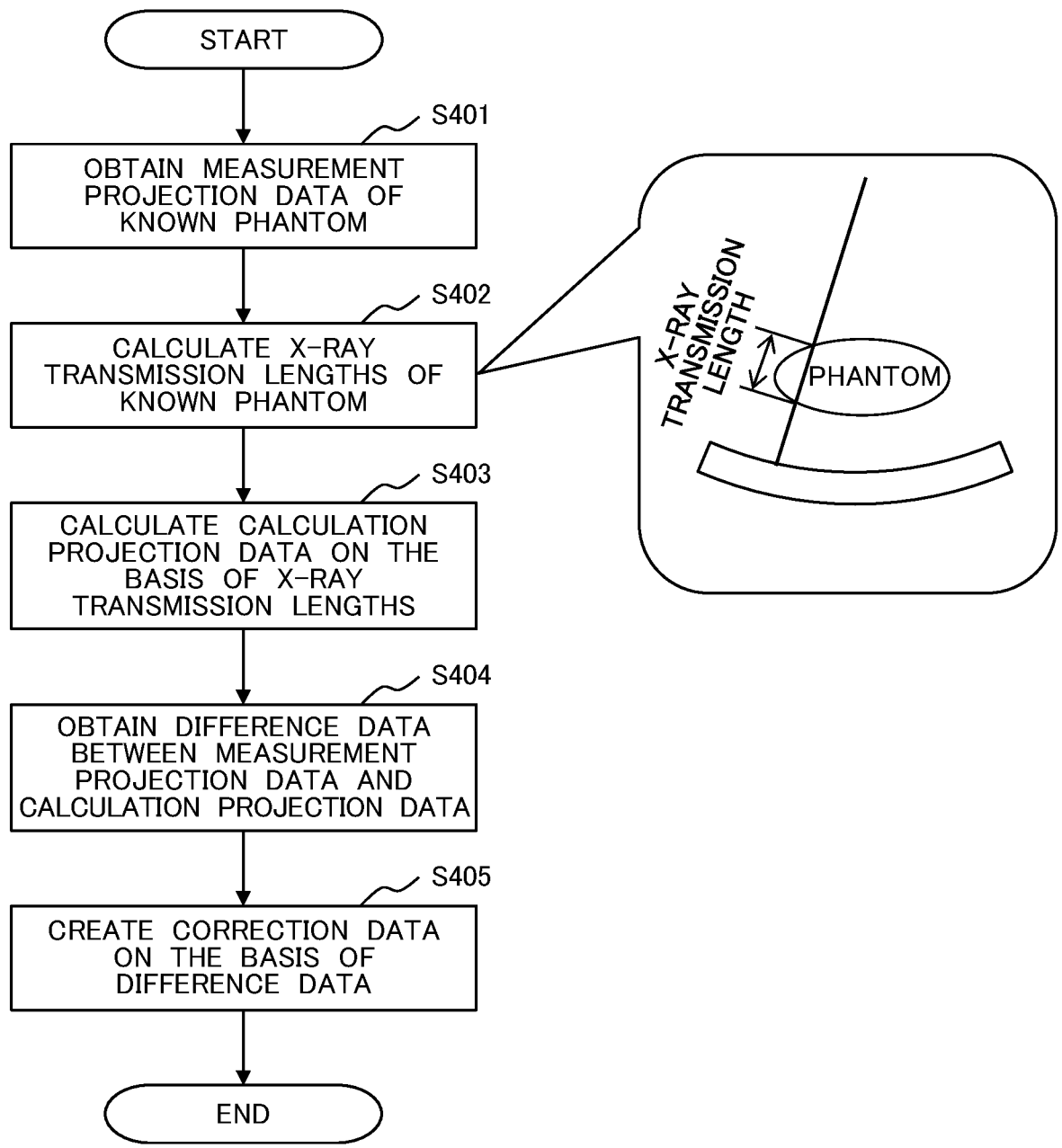
FIG. 4 is a diagram showing an example of the processing flow for creating correction data.

An example of a processing flow for creating the correction data will be explained step by step with reference to FIG. 4.
(S401)
The operation device 109 obtains measurement projection data for each X-ray energy by photographing a phantom having a known composition and a known shape.

Figure 5:
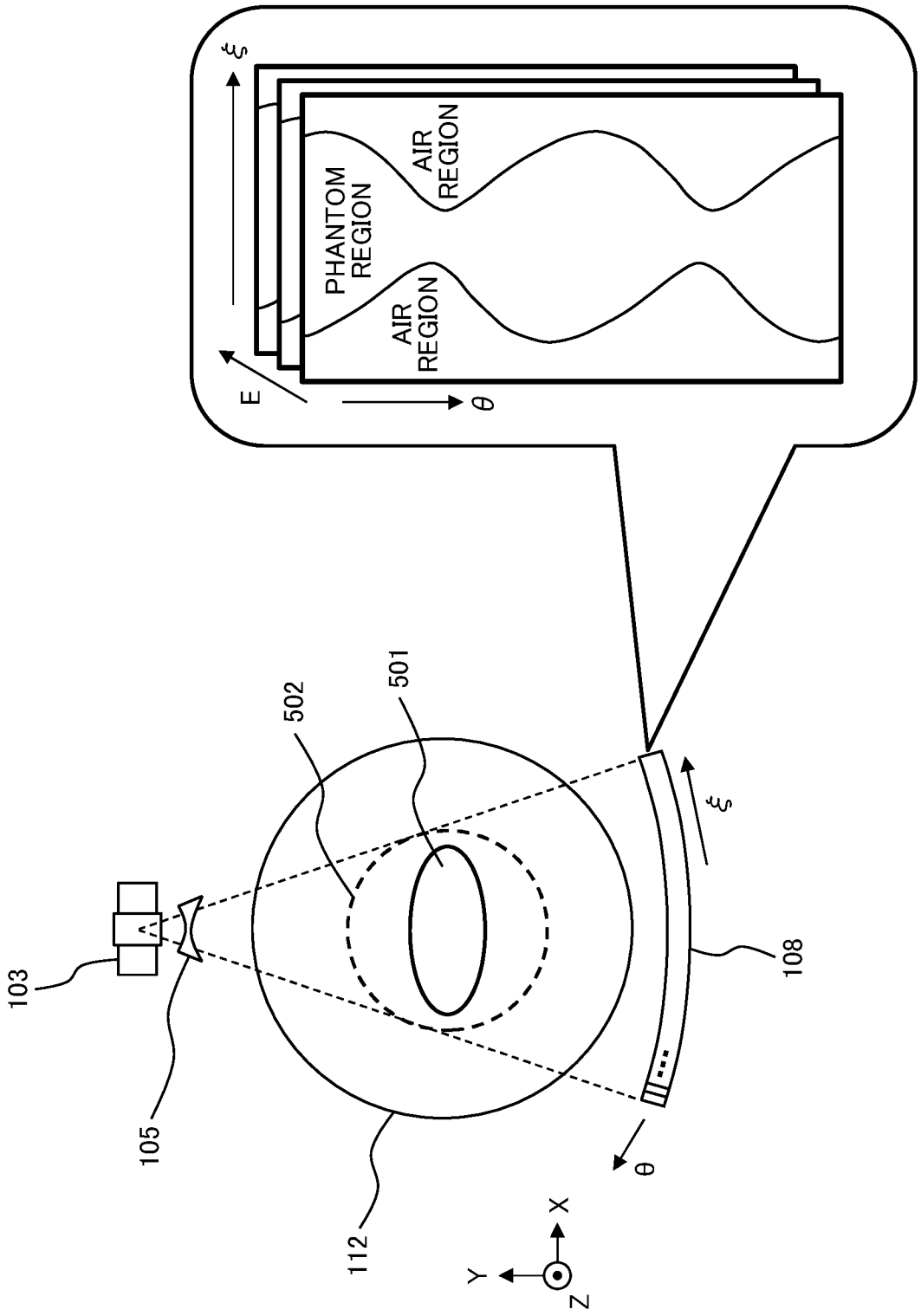
FIG. 5 is a diagram explaining the measured projection data of a phantom having a known composition and a known shape.

The measurement projection data of a phantom having a known composition and a known shape will be explained with reference to FIG. 5. A known phantom 501, which is a phantom having a known composition and a known shape, is disposed at the center of an opening 112 and photographed. As the known phantom 501, a material having a relatively small effective atomic number is used in accordance with the soft tissue of a human body. In addition, it is desirable that the known phantom 501 has an elliptical shape similar to the cross-sectional shape of the test subject 107. Furthermore, in order to simulate the head of the test subject 107, the outer surface portion of the known phantom 501 having an elliptical shape may be composed of a material having a relatively large effective atomic number.

Since the known phantom 501 is photographed while being rotated, measurement projection data including projection values that are mapped on a plane having the projection angle $\theta$ and the channel number $\xi$ of the detector panel 108 as variables on the coordinate axes of the plane is obtained. Since the detector panel 108 is composed of plural photon counting type detectors, projection data is obtained for each X-ray energy E. Here, the size of the known phantom 501 is smaller than the photographing field of view 502 of the X-ray CT apparatus 101. Since the size of the known phantom 501 is smaller than the photographing field of view 502, the influences of half shadows and scattered rays generated in the vicinity of the edge portion of the test subject 107 are included in the measurement projection data.

In addition, errors Δx and Δy between the center of the known phantom 501 and the rotation center of the gantry 102 and the slope Δθ of the known phantom 501 with respect to the horizon line may be obtained using the measurement projection data. For example, by dividing a tomographic image, which is obtained through the image reconstruction of the measured projection data, into air regions and another region and by performing elliptic approximation on the borders between the air regions and another region, Δx, Δy, and Δθ can be obtained. Alternatively, Δx and Δy may be obtained using the center position of the maximum width and that of the minimum width in the ξ direction in the measurement projection data, and A may be obtained using projection angles θ respectively related to the maximum width and the minimum width in the direction.

(S402)

The operation device 109 calculates X-ray transmission lengths on the basis of the shape of the known phantom 501. An X-ray transmission length is the length of a distance that an X-ray incident on any detection element travels when crossing the known phantom 501, and each X-ray transmission length is calculated for a combination of each projection angle θ and each channel number ξ of the detector panel 108. An X-ray transmission length may be calculated on the basis of the next expressions.

$$\frac{x^2}{A^2} + \frac{y^2}{B^2} = 1 \qquad \text{[Expression 1]}$$

$$y = px + q \qquad \text{[Expression 2]}$$

$$x = \frac{-A^2 pq \pm \sqrt{(A^2 pq)^2 - (B^2 + A^2 p^2)A^2(q^2 - B^2)}}{B^2 + A^2 p^2} \qquad \text{[Expression 3]}$$

Here, Expression 1 is an expression that represents the surface of a known phantom 501 the shape of which is an ellipse, and Expression 1 is expressed in an xy coordinate system the origin of which is the center of the ellipse. Assuming that A>B, A is the length of the long axis of the ellipse, and B is the length of the short axis of the ellipse.

Expression 2 is an expression that represents a straight line connecting the focus of the X-ray and any detection element, and the values of the slope p and the intercept q of the straight line are obtained for a combination of each projection angle θ and each channel number ξ. Here, the errors Δx and Δy between the center of the known phantom 501 and the rotation center of the gantry 102 and the slope Δθ of the known phantom 501 with respect to the horizon line may be included in the slope p and the intercept q of Expression 2.

Expression 3 is an expression that gives the x coordinates of the intersection points of Expression 1 and Expression 2, and by substituting the x coordinates given by Expression 3 into Expression 2, the y coordinates of the intersection points of Expression 1 and Expression 2 are obtained. Assuming that the coordinate points of the two intersection points are represented by (x1, y1) and (x2, y2), an X-ray transmission length can be obtained as ((x1−x2)^2+(y1−y2)^2)^0.5. Here, if two real number solutions cannot be obtained from Expression 3, the ellipse and the straight line do not intersect with each other, so that the X-ray transmission length is zero. Furthermore, if p→∞, that is, if the straight line is parallel with the y axis, although Expression 2 and Expression 3 cannot be used exceptionally, the variable y is vanished, so that an X-ray transmission length can easily obtained.

(S403)

The operation device 109 calculates calculation projection data on the basis of the X-ray transmission lengths calculated in S402. For the calculation of the calculation projection data, the calibration data 204 that is X-ray energy spectra each of which is obtained for each thickness of a base material and the values of attenuation coefficients described in literatures are used. BY using the calibration data 204, the calculation accuracy of the calculation projection data is improved.

Since the vertical axis of an X-ray energy spectrum represents the number of X-ray photons, by using an X-ray energy spectrum corresponding to the thickness of a base material corresponding to an X-ray transmission length, the X-ray transmission length is converted into the number of X-ray photons for each X-ray energy. And by comparing the value obtained by the conversion with the number of X-ray photons of an X-ray energy spectrum in the case of the thickness of the base material being zero, calculation projection data that is a projection value for a combination of each projection angle θ and each channel number ξ of the detector panel 108 is obtained for each X-ray energy. Since the calculation projection data is calculated on the basis of the X-ray transmission lengths that are the lengths of distances that the X-rays incident on the relevant detection elements travel when the X-rays cross the known phantom 501 respectively, the influences of the half shadows and scattered rays generated in the vicinity of the edge portion are not included in the calculation projection data.

(S404)

The operation device 109 obtains difference data by calculating differences between the measurement projection data obtained in S401 and the calculation projection data calculated in S403. Since the influences of the half shadows and the scattered rays generated in the vicinity of the edge portion are included in the measurement projection data and not included in the calculation projection data, only the influences of the half shadows and scattered rays generated in the vicinity of the edge portion are included in the difference data.

Figure 6:
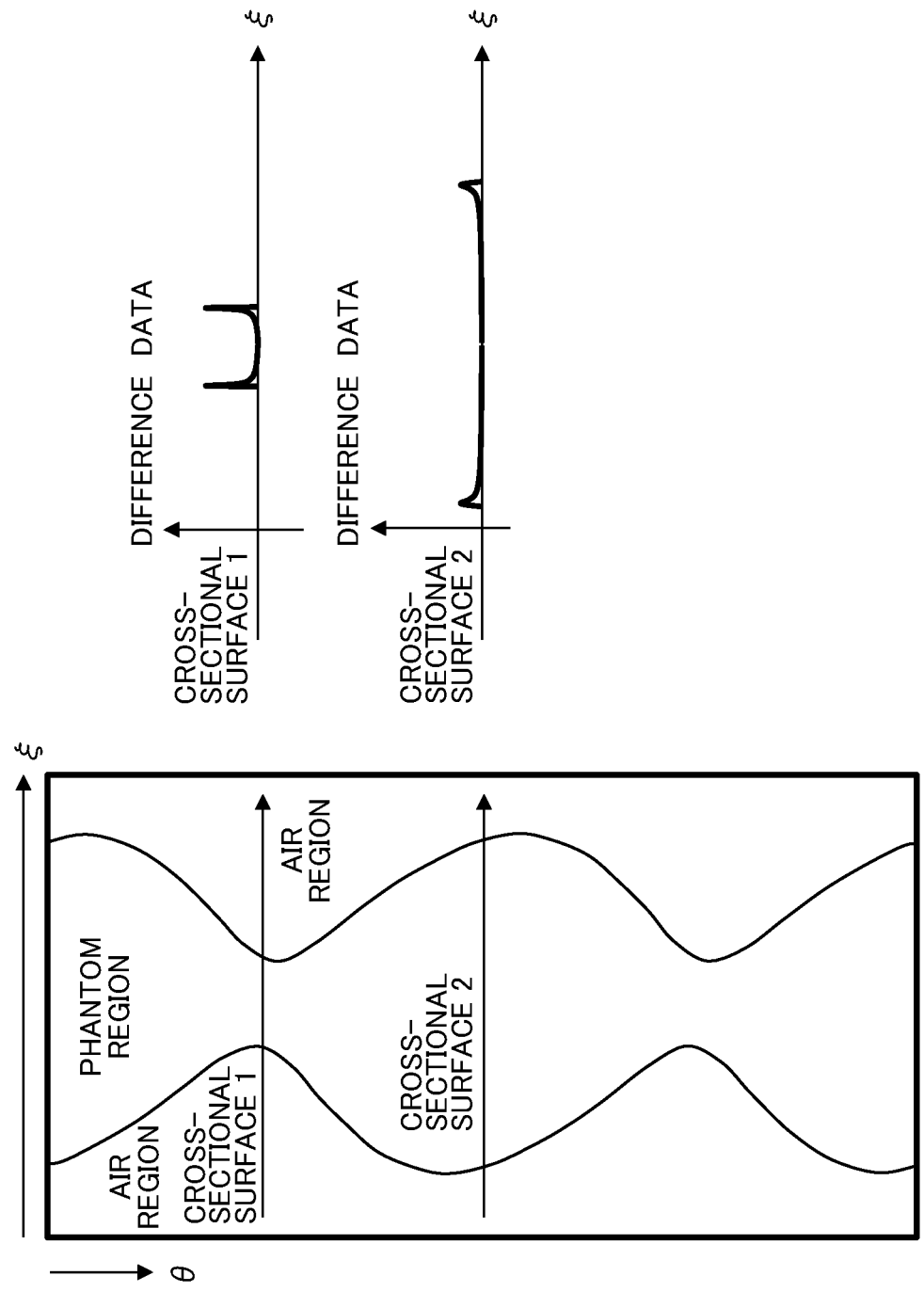
FIG. 6 is a diagram explaining difference data.

The difference data will be explained with reference to FIG. 6. The difference data shows the maximum value at a border between an air region and a phantom region, that is, at the edge element that is a detection element on which an X-ray passing through an edge portion is incident, and the difference data becomes smaller as the detection element on which an X-ray is incident approaches to the center of the known phantom 501 from the edge element. Owing to the half shadows generated because the X-ray focal point has a finite size, X-rays that passes through the air region are incident on detection elements near to the edge element, so that two sets of difference data as shown in FIG. 6 are obtained.

In addition, the value of difference data obtained at the edge element in a cross-sectional surface 1 including the edge portion of the short axis of the ellipse is larger than the value of difference data obtained at the edge element in a cross-sectional surface 2 including the edge portion of the long axis of the ellipse. Furthermore, the amount of change in difference data in the direction in the cross-sectional surface 1 is larger than that in the cross-sectional surface 2. These phenomena occur because the greater the attenuation change in the direction is, the greater the influences of the half shadows are.

(S405)

The operation device 109 creates correction data used for the correction of the projection data of the test subject 107 on the basis of the difference data obtained in S404. For example, the correction data is created by associating the values of the difference data with distances between the edge element that is a detection element on which an X-ray passing through the edge portion of the test subject 107 is incident and correction elements that are detection elements to be corrected.

In addition, in order to improve the accuracy of the correction, it is conceivable that plural sets of difference data are obtained by executing S401 to S404 on known phantoms 501 with plural sizes, and each of the obtained plural sets of difference data is used as correction data corresponding to a subject 107 with the relevant size. In this case as well, the correction data is associated with a distance between the edge element and the relevant correction element.

Figure 7:
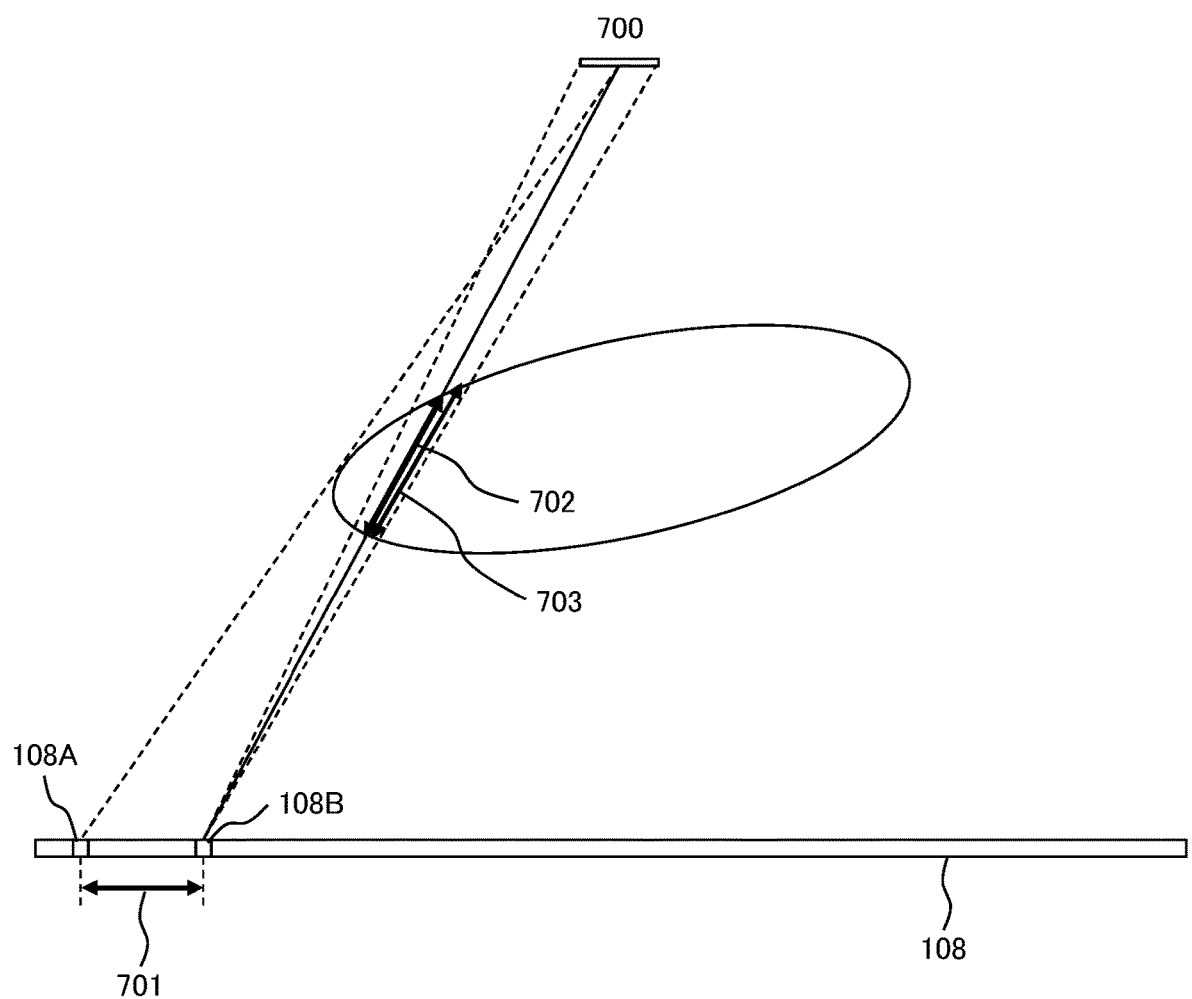
FIG. 7 is a diagram showing an example of an explanation variable.

Furthermore, it is conceivable that difference data obtained using a known phantom 501 with a single size is associated with a distance 701 between an edge element 108A and a correction element 108B shown in FIG. 7 and at the same time, the difference data is associated with an X-ray transmission length 702 related to the correction element 108B. As shown in FIG. 6, the greater the attenuation change in the direction is, the greater the influences of the half shadow are. Therefore, by associating the distance 701 and the X-ray transmission length 702 with the difference data, the influences of the half shadows are more accurately reflected in the difference data.

Here, when the distance 701 between the edge element 108A and the correction element 108B is close to zero, the X-ray transmission length 702 related to the correction element 108B also becomes close to zero, and the correction data is biased. Therefore, instead of the X-ray transmission length 702 related to the correction element 108B, the difference data may be associated with an alternative X-ray transmission length 703 that is an X-ray transmission length related to a detection element nearer to the center of the known phantom 501 than the correction element 108B. A distance between the detection element corresponding to the alternative X-ray transmission length 703 and the correction element 108B is preferably 1 to 3 mm.

The correction data created by associating difference data with distances between an edge element and correction elements and with X-ray transmission lengths related to the correction elements will be explained with reference to FIG. 8. In a graph on the left side of FIG. 8, the vertical axis represents an X-ray transmission length related to a correction element, the horizontal axis represents a distance from the edge element to a correction element, the axis orthogonal to the paper surface represents difference data, and diagonal lines in the graph represent a region in which difference data exists. In addition, in a graph on the right side of FIG. 8, difference data in a cross-sectional surface A and difference data in a cross-sectional B are shown. In the cross-sectional surface A and the cross-sectional surface B, the values of difference data are large in the vicinity of a place where distances from the relevant edge element to correction elements are close to zero, that is, in the vicinity of the relevant edge element. Furthermore, the cross-sectional surface B having large X-ray transmission lengths related to the correction elements has larger difference data values in the vicinity of the relevant edge portion than the cross-sectional surface A.

As explained above, the correction data is created by executing the processing flow explained with reference to FIG. 4, and the operation device 109 functions as a correction data creation unit for creating the correction data.

Figure 3:
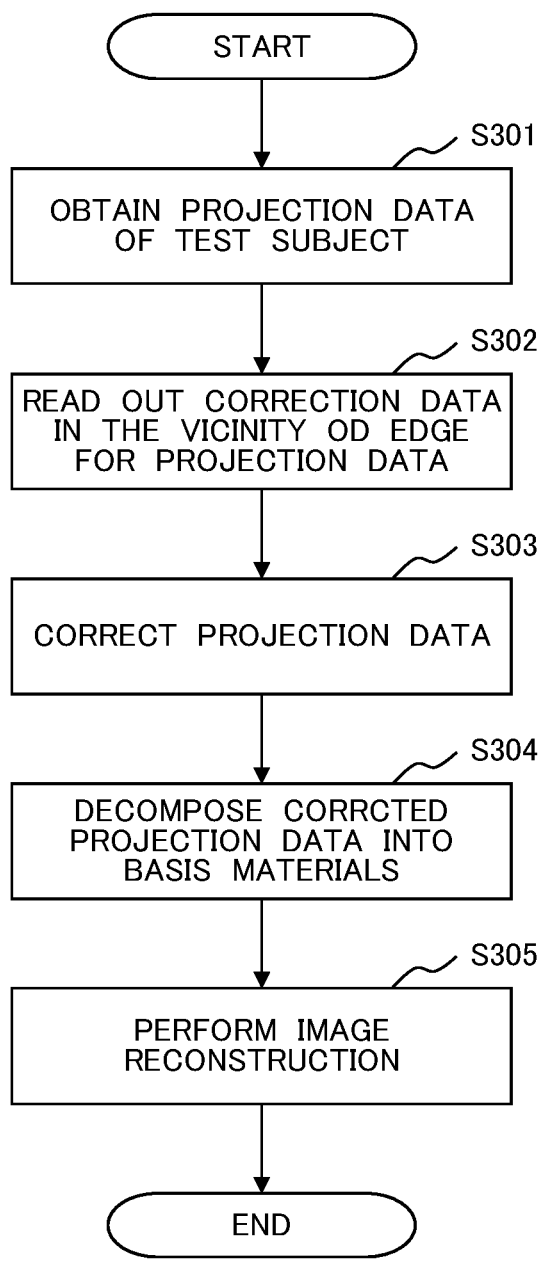
FIG. 3 is a diagram showing an example of the processing flow of a first embodiment.

The description returns to the explanation in FIG. 3.

(S303)

The operation device 109 corrects the projection data of the test subject 107 using the correction data obtained in S302. In other words, the operation device 109 functions as a correction unit for correcting the projection data of the test subject using the correction data.

Figure 9:
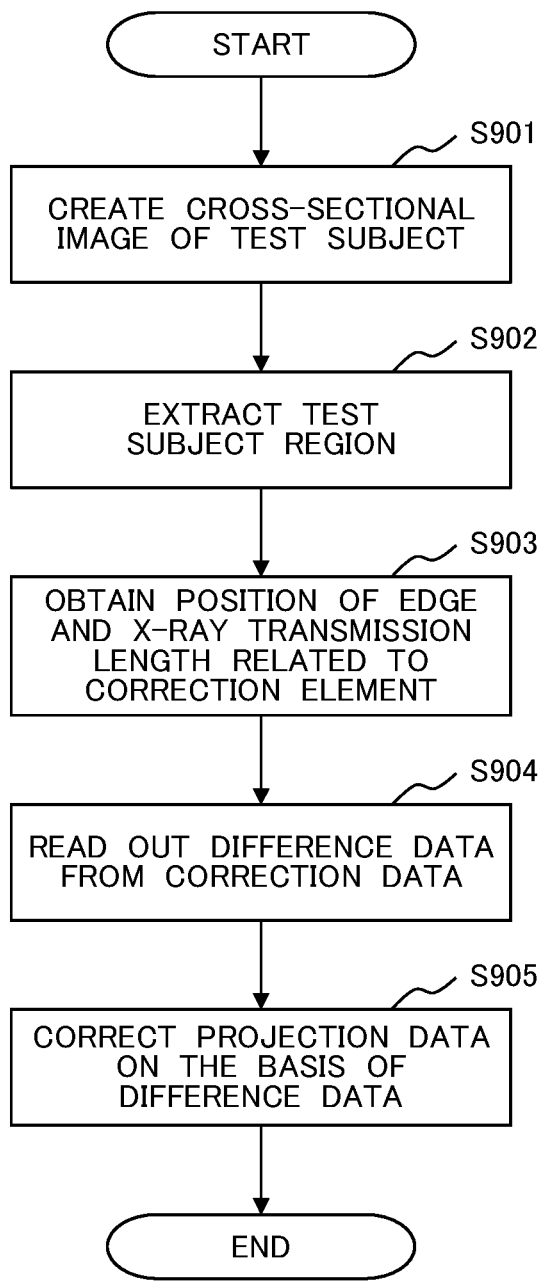
FIG. 9 is a diagram showing an example of the processing flow for correcting projection data.

An example of a processing flow for correcting the projection data will be explained step by step with reference to FIG. 9.

(S901)

The operation device 109 creates a cross-sectional image by performing image reconstruction on the projection data obtained in S301.

(S902)

The operation device 109 extracts a test subject region by binarizing the cross-sectional image created in S901.

(S903)

The operation device 109 obtains the position of an edge element and an X-ray transmission length related to a correction element on the basis of an X-ray transmission length for each coordinate point ($\xi$, $\theta$) that is obtained by performing a forward projection operation on the test subject region extracted in S902. Here, in the case where correction data is associated with an alternative X-ray transmission length 703, the alternative X-ray transmission length 703 is obtained on the basis of the X-ray transmission length obtained by the forward projection operation.

(S904)

Figure 8:
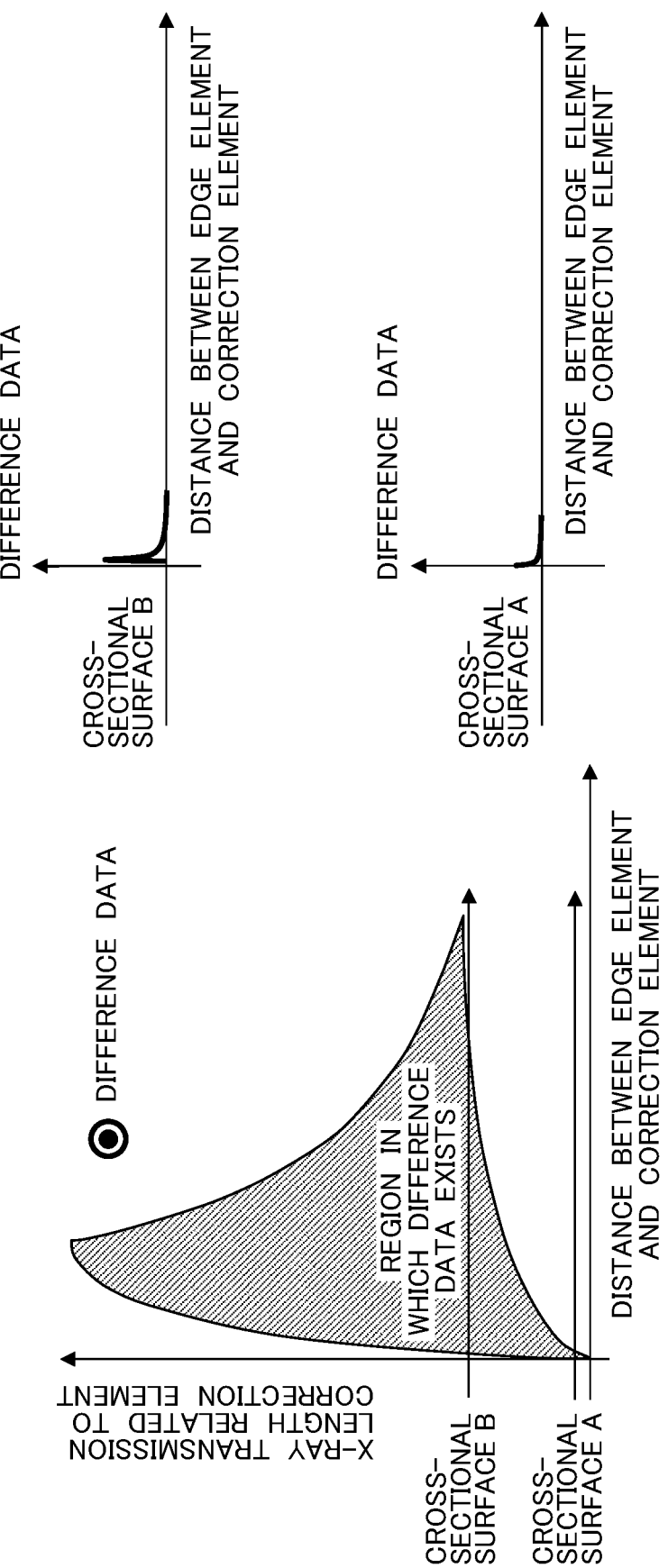
FIG. 8 is a diagram showing an example of correction data.

The operation device 109 reads out difference data from the correction data exemplified in FIG. 8 on the basis of the position of the edge element and the X-ray transmission length related to the correction element that are obtained in S903. In other words, difference data associated with a distance between the edge element and the correction element, and the X-ray transmission length related to the correction element is read out. Here, in the case where the correction data is associated with an alternative X-ray transmission length 703, the difference data is read out on the basis of the position of the edge element and the alternative X-ray transmission length 703.

(S905)

The operation device 109 corrects the projection data obtained in S301 on the basis of the difference data read out in S904. For example, if the difference data read out in S904 is data obtained by subtracting measurement projection data from calculation projection data, the correction is performed by adding the difference data to the projection data of the test subject. Corrected projection data that is the projection data corrected as mentioned above is obtained for each X-ray energy.

The description returns to the explanation in FIG. 3.

(S304)

The operation device 109 decomposes the corrected projection data obtained in S303 into base materials. For the decomposition into the base materials, the calibration data 204 is used, for example. The corrected projection data obtained for each X-ray energy has an X-ray energy spectrum for each coordinate point ($\xi$, $\theta$). An X-ray energy spectrum that is the closest to an X-ray energy spectrum for each coordinate point ($\xi$, $\theta$) is searched for among the X-ray energy spectra of the calibration data 204, and a thickness combination 201 of a base material combination corresponding to the searched-for X-ray energy spectrum is obtained. In other words, if the first base material 202 is acrylic, and the second base material 203 is tin, a thickness of acrylic and a thickness of tin are obtained for each coordinate point (ξ, θ), so that projection data of acrylic and projection data of tin are obtained.

(S305)

The operation device 109 performs image reconstruction on the projection data for each of the base materials decomposed in S304, and creates a tomographic image for each of the base materials.

As explained above, by executing the processing flow explained with reference to FIG. 3, a tomographic image with suppressed artifacts in the vicinity of the edge portion of a test subject can be created.

Examples of an X-ray CT apparatus and a correction method of projection data according to the present invention have been described above. The X-ray CT apparatus and the correction method of projection data according to the present invention are not limited to the above-described examples, and the X-ray CT apparatus and the correction method of projection data can be materialized by modifying the relevant components without departing from the gist of the present invention. In addition, plural components disclosed in the above embodiment may be appropriately combined. Furthermore, some of all the components disclosed in the above embodiment may be deleted.

REFERENCE SIGNS LIST

101: X-ray CT apparatus, 102: gantry, 103: X-ray tube, 104: X-ray, 105: bow tie filter, 106: berth, 107: test subject, 108: detector panel, 109: operation device, 110: input device, 111: display device, 112: opening, 201: combination of base materials, 202: first base material, 203: second base material, 204: calibration data, 501: known phantom, 502: photographing field of view, 701: distance between edge element and correction element, 702: X-ray transmission length related to correction element, 703: alternative X-ray transmission length

What is claimed is:

1. An X-ray CT apparatus for photographing a test subject comprising:
    a correction data creation unit that creates correction data using difference data between measurement projection data for each X-ray energy obtained by photographing a known phantom having a known composition, a known shape, and a size smaller than a photographing field of view of the X-ray CT apparatus and calculation projection data for each X-ray energy calculated on the basis of X-ray transmission lengths obtained from the shape of the known phantom; and
    a correction unit that corrects projection data for each X-ray energy of the test subject using the correction data.

2. The X-ray CT apparatus according to claim 1, wherein the correction data is associated with distances between an edge element that is a detection element on which an X-ray passing through an edge portion of the test subject is incident and correction elements that are detection elements to be corrected.

3. The X-ray CT apparatus according to claim 2, wherein the correction data is associated with the transmission lengths of X-rays incident on the correction elements.

4. The X-ray CT apparatus according to claim 1, wherein the correction data creation unit calculates the calculation projection data using calibration data for each X-ray energy obtained by photographing a board material with known composition and thickness.

5. The X-ray CT apparatus according to claim 1, wherein the known phantom has an elliptical shape.

6. The X-ray CT apparatus according to claim 5, wherein the known phantom includes: a first base material having an elliptical shape; and a second base material that has a larger effective atomic number than the first base material and surrounds an outer periphery of the first base material.

7. A correction method of projection data obtained by an X-ray CT apparatus for photographing a test subject comprising the steps of:
    creating correction data using difference data between measurement projection data for each X-ray energy obtained by photographing a known phantom having a known composition, a known shape, and a size smaller than a photographing field of view of the X-ray CT apparatus and calculation projection data for each X-ray energy calculated on the basis of X-ray transmission lengths obtained from the shape of the known phantom; and
    correcting projection data for each X-ray energy of the test subject using the correction data.

* * * * *